(12) United States Patent
Kaita et al.

(10) Patent No.: US 11,499,932 B2
(45) Date of Patent: Nov. 15, 2022

(54) GAS SENSOR

(71) Applicant: TDK Corporation, Tokyo (JP)

(72) Inventors: Yoshio Kaita, Tokyo (JP); Yutaka Matsuo, Tokyo (JP)

(73) Assignee: TDK CORPORATION, Tokyo (JP)

( * ) Notice: Subject to any disclaimer, the term of this patent is extended or adjusted under 35 U.S.C. 154(b) by 305 days.

(21) Appl. No.: 16/649,558

(22) PCT Filed: Sep. 5, 2018

(86) PCT No.: PCT/JP2018/032832
§ 371 (c)(1),
(2) Date: Mar. 20, 2020

(87) PCT Pub. No.: WO2019/065127
PCT Pub. Date: Apr. 4, 2019

(65) Prior Publication Data
US 2021/0003525 A1    Jan. 7, 2021

(30) Foreign Application Priority Data

Sep. 26, 2017  (JP) .............................. JP2017-184266
Jul. 9, 2018   (JP) .............................. JP2018-129769

(51) Int. Cl.
*G01N 27/12*   (2006.01)
*G01N 27/18*   (2006.01)
*G01N 33/00*   (2006.01)

(52) U.S. Cl.
CPC ......... *G01N 27/124* (2013.01); *G01N 27/122* (2013.01); *G01N 27/125* (2013.01);
(Continued)

(58) Field of Classification Search
CPC .... G01N 27/18; G01N 27/122; G01N 27/124; G01N 27/125; G01N 33/0031; G01N 33/004; G01N 33/006
See application file for complete search history.

(56) References Cited

U.S. PATENT DOCUMENTS

| | | |
|---|---|---|
| 4,882,287 A | 11/1989 | Holter et al. |
| 2003/0131653 A1 | 7/2003 | Bair et al. |
| 2009/0038289 A1* | 2/2009 | Oh-Hori .............. G01N 27/122 60/285 |

FOREIGN PATENT DOCUMENTS

| | | |
|---|---|---|
| JP | 51-140793 A | 12/1976 |
| JP | 58-011847 A | 1/1983 |

(Continued)

OTHER PUBLICATIONS

International Search Report issued in corresponding International Patent Application No. PCT/JP2018/032832, dated Oct. 30, 2018, with English translation.

*Primary Examiner* — Benjamin R Schmitt
(74) *Attorney, Agent, or Firm* — McDermott Will & Emery LLP

(57) ABSTRACT

A gas sensor includes: a first thermistor having a resistance value that changes according to a concentration of a first gas with a first sensitivity and changes according to a concentration of a second gas with a second sensitivity; a second thermistor connected in series to the first thermistor, the second thermistor having a resistance value that changes according to a concentration of the first gas with a third sensitivity that is lower than the first sensitivity and changes according to a concentration of the second gas with a fourth sensitivity that is different from the second sensitivity; and a correction resistor connected in parallel with the first or second thermistor.

8 Claims, 13 Drawing Sheets

(52) U.S. Cl.
    CPC ............ *G01N 27/18* (2013.01); *G01N 33/004* (2013.01); *G01N 33/006* (2013.01); *G01N 33/0031* (2013.01)

(56) References Cited

FOREIGN PATENT DOCUMENTS

| JP | S5811847 A | * | 1/1983 | ............ G01N 27/12 |
|----|------------|---|--------|----------|
| JP | 58-158550 A | | 9/1983 | |
| JP | 63-500541 A | | 2/1988 | |
| JP | 2011-133401 A | | 7/2011 | |
| JP | 2016-170161 A | | 9/2016 | |

* cited by examiner

GAS SENSOR

CROSS REFERENCE

This application is the U.S. National Phase under 35 U.S.C. § 371 of International Application No. PCT/JP2018/032832, filed on Sep. 5, 2018, which claims the benefit of Japanese Patent Application No. 2017-184266, filed on Sep. 26, 2017 and Japanese Patent Application No. 2018-129769, filed Jul. 9, 2018, the entire contents of each are hereby incorporated by reference.

TECHNICAL FIELD

The present invention relates to a gas sensor for detecting gas contained in the atmosphere and, more particularly, to a gas sensor capable of canceling the influence of a gas different from a detection target gas.

BACKGROUND ART

A gas sensor detects the concentration of a measurement target gas contained in the atmosphere, but a measurement error may occur due to the influence of a gas contained in the atmosphere that is different from the detection target gas. Patent Document 1 discloses a method of correcting a signal obtained from a hydrogen sensor unit that detects a hydrogen gas as the detection target, based on oxygen concentration and/or humidity obtained respectively from an oxygen concentration measurement part and/or a humidity measurement part which are provided separately from the hydrogen sensor unit.

CITATION LIST

Patent Document

[Patent Document 1] JP 2011-133401A

SUMMARY OF THE INVENTION

[Problem to be Solved by the Invention]

However, with the method disclosed in Patent Document 1, there is a necessity of performing computation processing for calculation of the gas concentration. In addition, the oxygen concentration measurement part and/or a humidity measurement part are provided outside the hydrogen sensor unit, so that not only the size of the entire sensor is increased, but also it is difficult to perform accurate correction.

It is therefore an object of the present invention is to provide a gas sensor capable of highly accurately eliminating the influence of a gas different from a detection target gas without performing computation processing.

[Means for Solving the Problem]

A gas sensor according to the present invention includes: a first thermistor having a resistance value that changes according to a concentration of a first gas with a first sensitivity and changes according to a concentration of a second gas with a second sensitivity; a second thermistor connected in series to the first thermistor, the second thermistor having a resistance value that changes according to a concentration of the first gas with a third sensitivity that is lower than the first sensitivity and changes according to a concentration of the second gas with a fourth sensitivity that is different from the second sensitivity; and a correction resistor connected in parallel with the first or second thermistor to cancel a change in potential at a connection point between the first and second thermistors according to the concentration of the second gas.

According to the present invention, the first and second thermistors are connected in series to each other, and a change in potential at the connection point between the first and second thermistors according to the concentration of the second gas is canceled by the correction resistor, so that it is possible to easily and highly accurately eliminate the influence of the second gas without requiring computation processing, allowing accurate computation of the concentration of the first gas.

In the present invention, the first thermistor may be heated to a first temperature by a first heater, and the second thermistor may be heated to a second temperature different from the first temperature by a second heater. With this configuration, for example, the first and second thermistors can have the same configuration.

In the present invention, the fourth sensitivity may be higher than the second sensitivity, and the correction resistor may be connected parallel to the second thermistor. With this configuration, the fourth sensitivity is effectively reduced and can thus be made to coincide with the second sensitivity.

In the present invention, assuming that the second sensitivity is a, the fourth sensitivity is b, and the resistance value of the second thermistor heated to the second temperature is $Rd2$, the resistance value $R1$ of the correction resistor may be defined as: $R1=(b/a) \times Rd2$. This makes it possible to substantially completely eliminate the influence of the second gas.

The gas sensor according to the present invention may further include a third thermistor disposed between the first thermistor and the second thermistor. With this configuration, a distance between the first thermistor and the second thermistor is increased, making it possible to reduce mutual thermal interference therebetween.

The gas sensor according to the present invention may further include a control part that changes first and second control voltages to be supplied respectively to the first and second heaters according to a temperature signal supplied from the third thermistor. With this configuration, it is possible to set heating temperatures by the first and second heaters to values substantially the same as designed temperatures irrespective of the current environmental temperature.

The gas sensor according to the present invention may further include a first heater that heats the first thermistor to a first temperature, a second heater that heats the second thermistor to a second temperature, a first amplifier that receives a common control voltage and applies a first control voltage to the first heater, and a second amplifier that receives the common control voltage and applies a second control voltage to the second heater. With this configuration, it is possible to reduce a measurement error due to a fluctuation of a power supply potential.

In the present invention, the third sensitivity may be 1/10 or less of the first sensitivity. This allows the concentration of the first gas to be computed more accurately.

In the present invention, the first thermistor and second thermistor may be housed in the same package. This makes measurement conditions for the first and second thermistors coincide with each other, allowing the influence of the second gas to be removed more accurately.

In the present invention, the first and second thermistors may constitute a heat conduction type sensor. It is difficult to achieve a high detection sensitivity with the heat conduction type sensor, and thus a detection error tends to be large;

however, according to the present invention, it is possible to reduce a detection error due to a gas different from a detection target gas.

In the present invention, the first gas may be a $CO_2$ gas, and the second gas may be vapor. Thus, it is possible to eliminate the influence of humidity in the detection of $CO_2$ gas concentration.

[Advantageous Effects of the Invention]

Thus, according to the present invention, it is possible to highly accurately eliminate the influence of a gas different from a detection target gas without performing computation processing, thus allowing the concentration of the detection target gas to be highly accurately measured.

BRIEF DESCRIPTION OF DRAWINGS

FIG. 6A illustrates a change in the $CO_2$ gas and a change in humidity, and FIG. 6B illustrates a change in the detection signal Vout1.

MODE FOR CARRYING OUT THE INVENTION

Preferred embodiments of the present invention will be explained below in detail with reference to the accompanying drawings.

Figure 1:
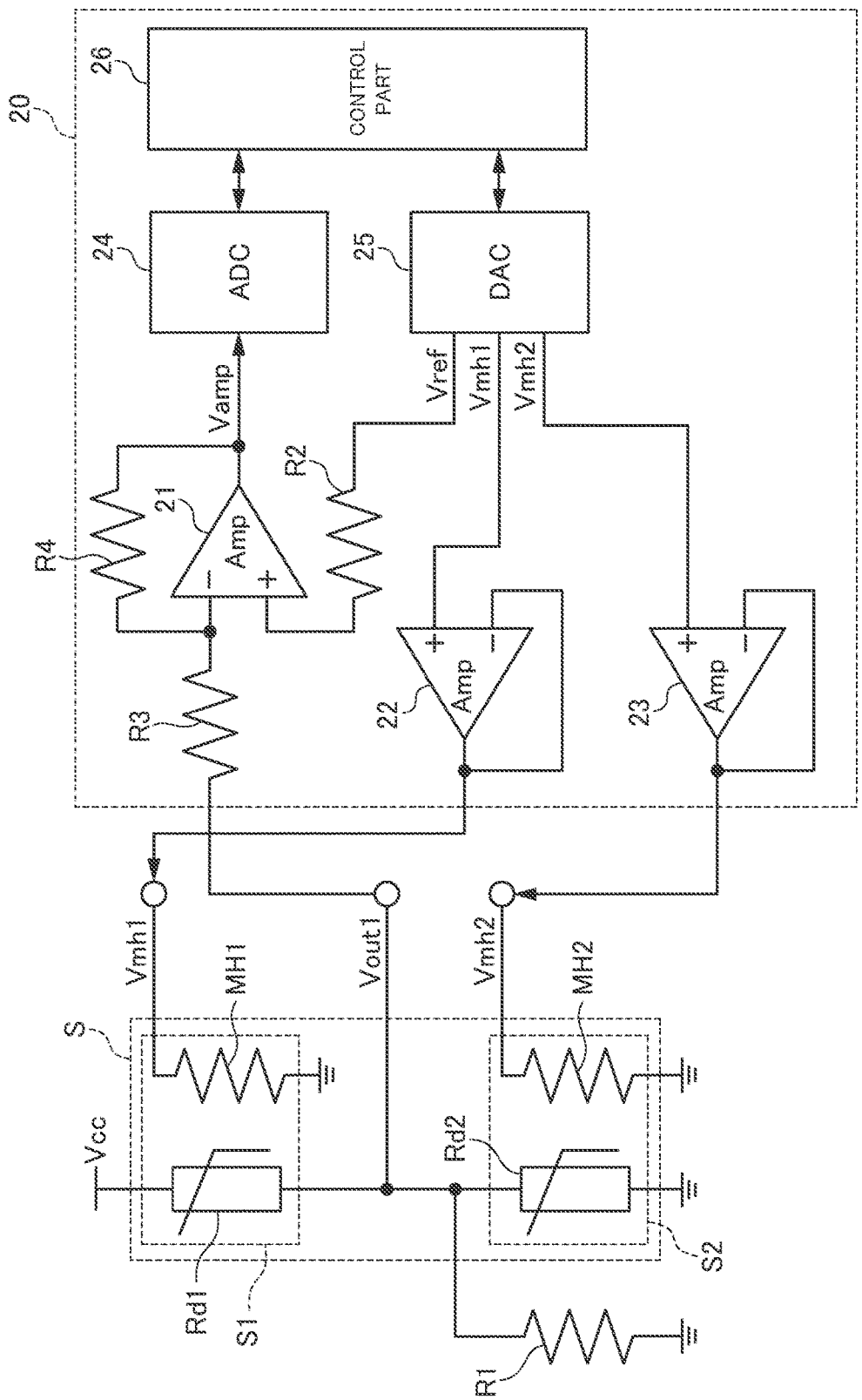
FIG. 1 is a circuit diagram illustrating the configuration of a gas sensor 10A according to a first embodiment of the present invention.

FIG. 1 is a circuit diagram illustrating the configuration of a gas sensor 10A according to the first embodiment of the present invention.

As illustrated in FIG. 1, the gas sensor 10A according to the present embodiment has a sensor part S and a signal processing circuit 20. Although not particularly limited, the gas sensor 10A according to the present embodiment detects the concentration of a $CO_2$ gas in the atmosphere and can cancel a measurement error due to humidity by hardware as will be described later. In the present specification, a detection target gas and a gas to become noise are sometimes referred to as "first gas" and "second gas", respectively. In the present embodiment, the first gas is a $CO_2$ gas, and the second gas is vapor.

The sensor part S is a heat conduction type gas sensor for detecting the concentration of a $CO_2$ gas to be detected and has a first sensor part S1 and a second sensor part S2. The first sensor part S1 includes a first thermistor Rd1 and a first heater resistor MH1 that heats the first thermistor Rd1. Similarly, the second sensor part S2 includes a second thermistor Rd2 and a second heater resistor MH2 that heats the second thermistor Rd2. As illustrated in FIG. 1, the first and second thermistors Rd1 and Rd2 are connected in series to each other between a wiring supplied with a power supply potential Vcc and a wiring supplied with a ground potential GND. The first and second thermistors Rd1 and Rd2 are each made of a material having a negative resistance temperature coefficient, such as a composite metal oxide, amorphous silicon, polysilicon, or germanium. The first and second thermistors Rd1 and Rd2 both detect the concentration of the $CO_2$ gas but differ in operating temperature as will be described later.

The first thermistor Rd1 is heated by the first heater resistor MH1. The heating temperature of the first thermistor Rd1 by the first heater resistor MH1 is, e.g., 150° C. When the $CO_2$ gas is present in the measurement atmosphere in a state where the first thermistor Rd1 is heated, heat dissipation characteristics of the first thermistor Rd1 changes according to the concentration of the $CO_2$ gas. This change appears as a change in the resistance value of the first thermistor Rd1. When the heating temperature of the first thermistor Rd1 is 150° C., the resistance value of the first thermistor Rd1 changes according to the $CO_2$ gas concentration with a first sensitivity. The first sensitivity has a sensitivity that can sufficiently change the potential of a detection signal Vout1 appearing at a connection point between the first and second thermistors Rd1 and Rd2.

When vapor is present in the measurement atmosphere in a state where the first thermistor Rd1 is heated, heat dissipation characteristics of the first thermistor Rd1 changes according to the concentration of the vapor. When the heating temperature of the first thermistor Rd1 is 150° C., the resistance value of the first thermistor Rd1 changes according to humidity with a second sensitivity.

The second thermistor Rd2 is heated by the second heater resistor MH2. The heating temperature of the second thermistor Rd2 by the second heater resistor MH2 is, e.g., 300° C. Even when the $CO_2$ gas is present in the measurement atmosphere in a state where the second thermistor Rd2 is heated, the resistance value of the second thermistor Rd2 hardly changes. That is, when the heating temperature of the second thermistor Rd2 is 300° C., the resistance value of the second thermistor Rd2 changes according to the $CO_2$ gas concentration with a third sensitivity; however, the third sensitivity is significantly lower than the first sensitivity and is preferably 1/10 or less of the first sensitivity, and more preferably, substantially 0. Thus, even when the $CO_2$ gas concentration changes, the resistance value of the second thermistor Rd2 hardly changes.

When vapor is present in the measurement atmosphere in a state where the second thermistor Rd2 is heated, heat dissipation characteristics of the second thermistor Rd2 changes according to the vapor concentration. When the heating temperature of the second thermistor Rd2 is 300° C., the resistance value of the second thermistor Rd2 changes according to humidity with a fourth sensitivity. The fourth sensitivity is higher than the second sensitivity.

Further, the gas sensor 10A according to the present embodiment has a correction resistor R1 connected parallel to the second thermistor Rd2. As described later, the correction resistor R1 is provided to cancel a difference between a sensitivity (second sensitivity) of the first thermistor Rd1 with respect to humidity and a sensitivity (fourth sensitivity) of the second thermistor Rd2 with respect to humidity.

As described above, the first and second thermistors Rd1 and Rd2 are connected in series to each other, and the detection signal Vout1 is output from the connection point therebetween. The detection signal Vout1 is input to the signal processing circuit 20.

The signal processing circuit 20 has differential amplifiers 21 to 23, an AD converter (ADC) 24, a DA converter (DAC) 25, a control part 26, and resistors R2 to R4. The differential amplifier 21 compares the detection signal Vout1 and a reference voltage Vref and amplifies the detected difference. The gain of the differential amplifier 21 is arbitrarily adjusted by the resistors R2 to R4. An amplified signal Vamp output from the differential amplifier 21 is input to the AD converter 24.

The AD converter 24 converts the amplified signal Vamp into a digital signal and supplies the obtained value to the control part 26. On the other hand, the DA converter converts a reference signal supplied from the control part 26 to an analog signal to generate the reference voltage Vref and generates control voltages Vmh1 and Vmh2 to be supplied respectively to the first and second heater resistors MH1 and MH2. The control voltage Vmh1 is applied to the first heater resistor MH1 through a differential amplifier 22 which is a voltage follower. Similarly, the control voltage Vmh2 is applied to the second heater resistor MH2 through a differential amplifier 23 which is a voltage follower.

Figure 2:
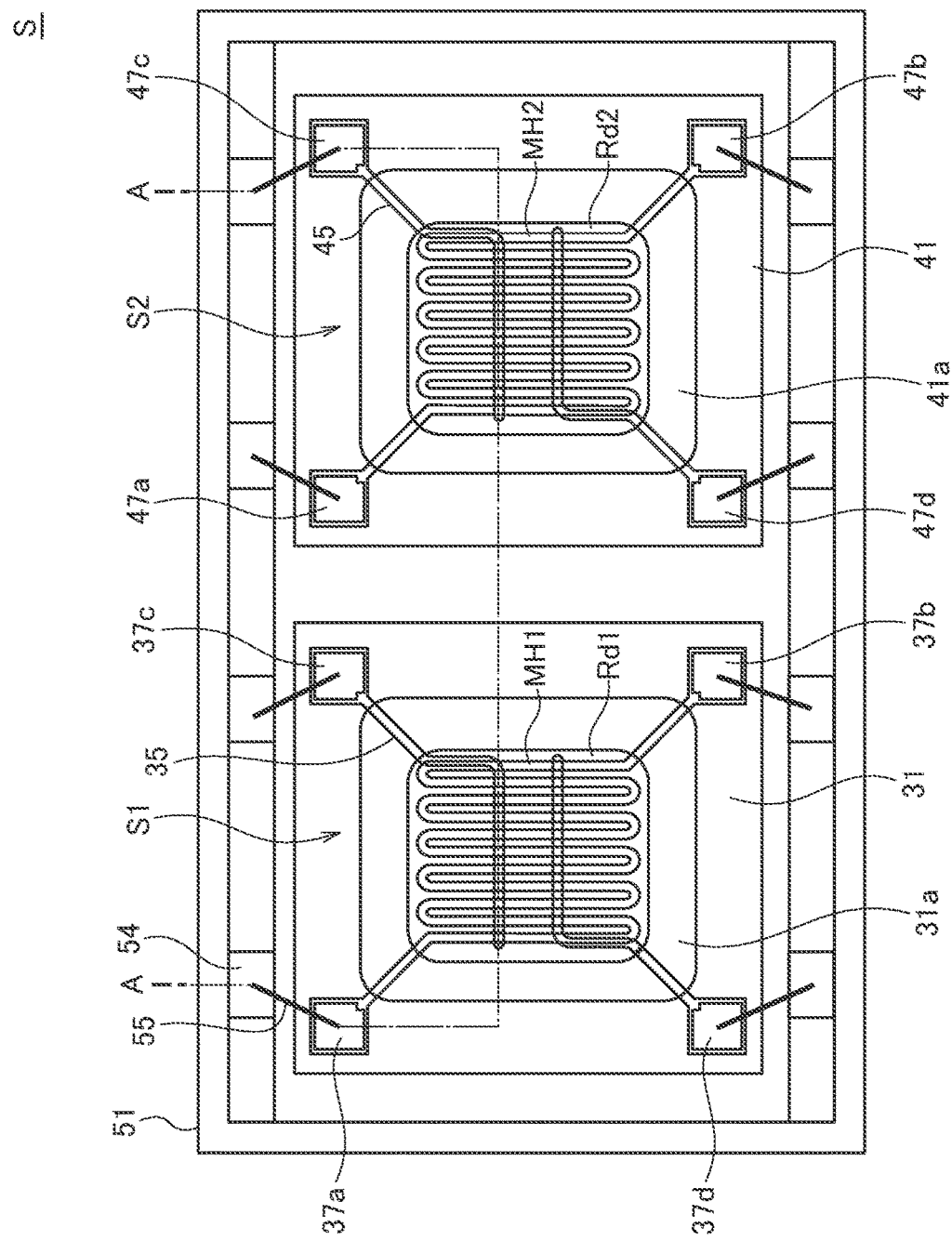
FIG. 2 is a top view for explaining the configuration of the sensor part S.
Figure 3:
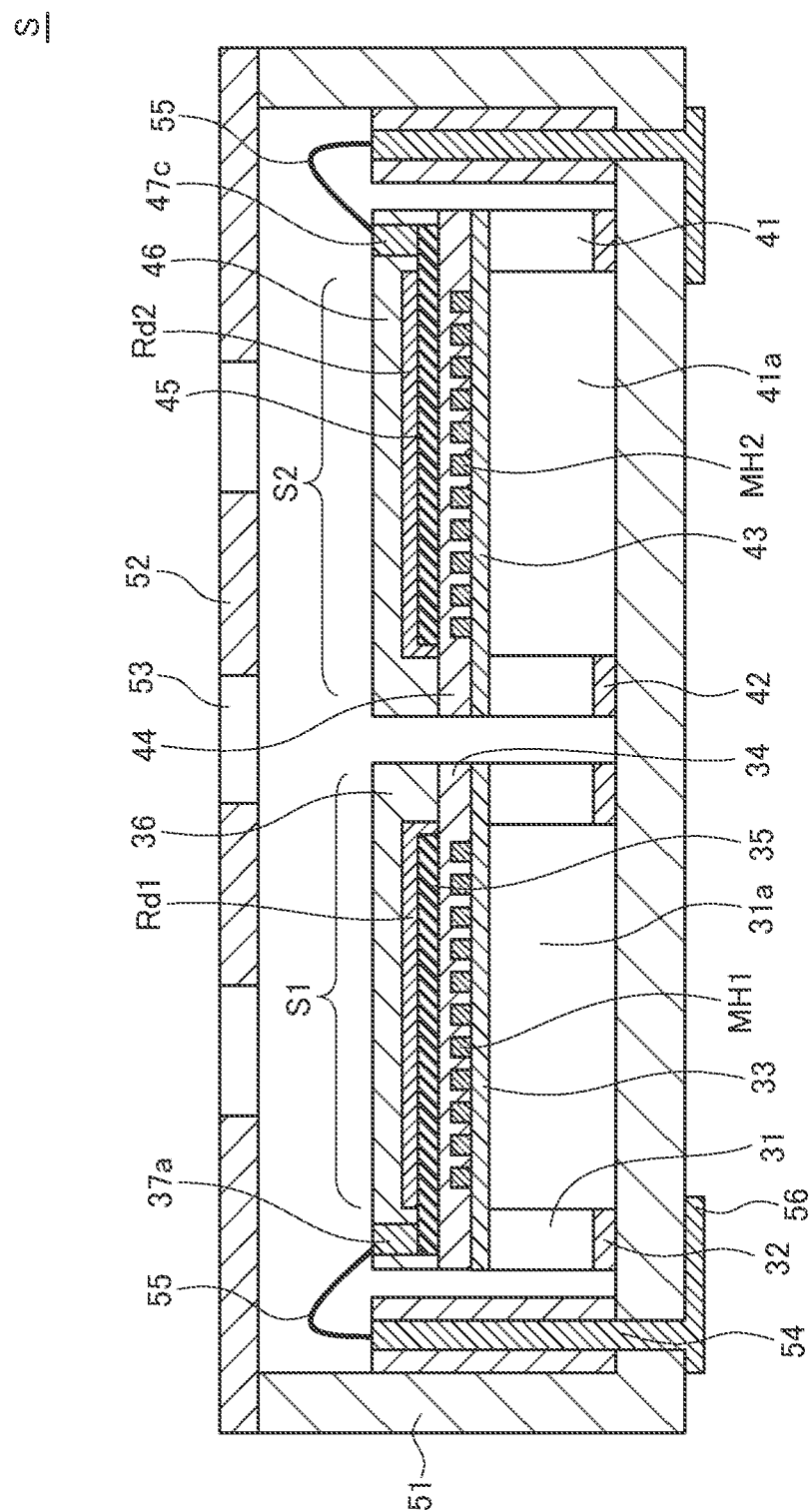
FIG. 3 is a cross-sectional view taken along line A-A in FIG. 2.

FIG. 2 is a top view for explaining the configuration of the sensor part S. FIG. 3 is a cross-sectional view taken along line A-A in FIG. 2. The drawings are schematic, and for explanatory convenience, the relation between thickness and plane dimension, ratio between the thicknesses of devices, and the like may be different from those in the actual structure within a range in which the effect of the present embodiment can be obtained.

The sensor part S is a heat conduction type gas sensor that detects the concentration of a gas based on a change in heat dissipation characteristics according to the $CO_2$ gas concentration and has, as illustrated in FIGS. 2 and 3, two sensor parts S1 and S2 and a ceramic package 51 housing the sensor parts S1 and S2.

The ceramic package 51 is a box-shaped case having an opened upper part, and a lid 52 is provided at the upper part. The lid 52 has a plurality of vent holes 53, through which $CO_2$ gas in the atmosphere can flow into the ceramic package 51. In FIG. 2, the lid 52 is omitted for ease of viewing.

The first sensor part S1 includes insulating films 32 and 33 formed respectively on the lower and upper surfaces of a substrate 31, a first heater resistor MH1 provided on the insulating film 33, a heater protective film 34 covering the first heater resistor MH1, a first thermistor Rd1 and a thermistor electrode 35 which are provided on the heater protective film 34, a thermistor protective film 36 covering the first thermistor Rd1 and thermistor electrode 35.

There is no particular restriction on the material of the substrate 31 as long as it has an adequate mechanical strength and is suitable for fine processing such as etching, and, examples thereof include a silicon single crystal substrate, a sapphire single crystal substrate, a ceramic substrate, a quartz substrate, a glass substrate, and the like. A cavity 31a is provided at a position overlapping the first heater resistor MH1 in a plan view so as to suppress conduction of heat due to the first heater resistor MH1 to the substrate 31. A part where the substrate 31 is removed by the cavity 31a is called a membrane. The presence of the membrane reduces heat capacity by the thinning of the substrate 31, allowing heating to be achieved with less power consumption.

The insulating films 32 and 33 are each made of an insulating material such as silicon oxide or silicon nitride. When silicon oxide is used as the insulating films 32 and 33, a film deposition method such as a thermal oxidation method or a CVD (Chemical Vapor Deposition) method may be used. There is no particular restriction on the thickness of the insulating films 32 and 33 as long as the insulating property thereof is ensured and may be, e.g., about 0.1 µm to 1.0 µm. Particularly, the insulating film 33 is used also as an etching stop layer when the cavity 31a is formed in the substrate 31, so that the thickness thereof is preferably set to a value suitable for fulfilling the function as the etching stop layer.

The first heater resistor MH1 is made of a conductive substance whose resistivity changes depending on temperature and is preferably made of a metal material having a comparatively high melting point, such as molybdenum (Mo), platinum (Pt), gold (Au), tungsten (W), tantalum (Ta), palladium (Pd), iridium (Ir), or an alloy containing two or more of them. Among them, a conductive material that can be subjected to high accuracy dry etching such as ion milling is preferable, and more preferably, it contains platinum (Pt) having high corrosion resistance as a main component. Further, an adhesion layer such as a titanium (Ti) layer is preferably formed as a base of Pt so as to improve adhesion with respect to the insulating film 33.

The heater protective film 34 is formed above the first heater resistor MH1. The heater protective film 34 is preferably made of the same material as the insulating film 33. The first heater resistor MH1 generates violent thermal changes (repetition of temperature rises between room temperature to 150° C. and then a drop to room temperature again), so that strong thermal stress is applied to the insulating film 33 and heater protective film 34. When being continuously subject to the thermal stress, the insulating film 33 and heater protective film 34 may suffer damage such as interlayer peeling or crack. However, when the insulating film 33 and the heater protective film 34 are made of the same material, material characteristics thereof are the same, and adhesion strength therebetween is high, so that the damage such as interlayer peeling or crack is less likely to occur as compared to when the insulating film 33 and the heater protective film 34 are made of mutually different materials. When silicon oxide is used as the material of the heater protective film 34, film deposition may be performed by a thermal oxidation method or a CVD method. The film thickness of the heater protective film 34 is not particularly restricted as long as insulation between the first thermistor Rd1 and the thermistor electrode 35 can be ensured and may be, e.g., 0.1 µm to 3.0 µm.

The first thermistor Rd1 is made of a material having a negative resistance-temperature coefficient, such as a composite metal oxide, amorphous silicon, polysilicon, or germanium and can be formed by using a thin-film process such as a sputtering method or a CVD method. The film thickness of the first thermistor Rd1 may be adjusted according to a target resistance value. For example, when the resistance value (R25) at room temperature is set to about 2 MSΩ using MnNiCo based oxide, the film thickness may be set to about 0.2 µm to 1 µm although it depends on the distance between a pair of thermistor electrodes 35. The reason that the thermistor is used as a temperature-sensitive resistive element is that the thermistor is larger in resistance temperature coefficient than a platinum temperature detector and can thus obtain high detection sensitivity. Further, heat generation of the first heater resistor MH1 can efficiently be detected because of the thin-film structure.

The thermistor electrode 35 is configured of a pair of electrodes arranged spaced apart from each other at a predetermined interval, and the first thermistor Rd1 is provided between the pair of thermistor electrodes 35. With this configuration, the resistance value between the pair of thermistor electrodes 35 is determined by the resistance value of the first thermistor Rd1. The thermistor electrode 35 may be made of a conductive substance that can endure a process such as a film deposition step and a heat treatment process for the first thermistor Rd1 and is preferably made of a material having a comparatively high melting point, such as molybdenum (Mo), platinum (Pt), gold (Au), tungsten (W), tantalum (Ta), palladium (Pd), iridium (Ir), or an alloy containing two or more of them.

The first thermistor Rd1 and thermistor electrode 35 are covered with the thermistor protective film 36. When the first thermistor Rd1 is brought into contact with a material having reducibility so as to make it turn into a high-temperature state, the material deprives the thermistor of oxygen to cause a reduction, thus affecting thermistor characteristics. To prevent this, an insulating oxide film having no reducibility, such as silicon oxide film, is preferably used as the material of the thermistor protective film 36.

As illustrated in FIG. 2, both ends of the first heater resistor MH1 are connected respectively to electrode pads 37a and 37b provided on the surface of the thermistor protective film 36. Further, both ends of the thermistor electrode 35 are connected respectively to electrode pads 37c and 37d provided on the surface of the thermistor protective film 36. The electrode pads 37a to 37d are connected to a package electrode 54 installed to the ceramic package 51 through a bonding wire 55. The package electrode 54 is connected to the signal processing circuit 20 illustrated in FIG. 1 through an external terminal 56 provided on the back surface of the ceramic package 51.

As described above, the first sensor part S1 has a configuration in which the first heater resistor MH1 and first thermistor Rd1 are laminated on the substrate 31, so that heat generated by the first heater resistor MH1 is efficiently conducted to the first thermistor Rd1.

Similarly, the second sensor S2 includes insulating films 42 and 43 formed respectively on the lower and upper surfaces of a substrate 41, a second heater resistor MH2 provided on the insulating film 43, a heater protective film 44 covering the second heater resistor MH2, a second thermistor Rd2 and a thermistor electrode 45 which are provided on the heater protective film 44, and a thermistor protective film 46 covering the second thermistor Rd2 and thermistor electrode 45.

The substrate 41 is made of the same material as the substrate 31 used for the first sensor part S1 and has the same configuration as the substrate 31. That is, a cavity 41a is provided at a position overlapping the second heater resistor MH2 in a plan view so as to suppress heat due to the second heater resistor MH2 from conducting to the substrate 41. The insulating films 42 and 43 are made of the same material (insulating material such as silicon oxide or silicon nitride) as the insulating films 32 and 33. The insulating films 42 and 43 have the same thickness as the insulating films 32 and 33.

The second heater resistor MH2, heater protective film 44, second thermistor Rd2, thermistor electrode 45, and thermistor protective film 46 have the same configurations as the first heater resistor MH1, the heater protective film 34, the first thermistor Rd1, the thermistor electrode 35, and the thermistor protective film 36, respectively, used for the first sensor part 51. Both ends of the second heater resistor MH2 are connected respectively to electrode pads 47a and 47b provided on the surface of the thermistor protective film 46.

Further, the both ends of the thermistor electrode 45 are connected respectively to electrode pads 47c and 47d provided on the surface of the thermistor protective film 46. The electrode pads 47a to 47d are connected to the package electrode 54 fitted in the ceramic package 51 through the bonding wire 55.

The thus configured first and second sensor parts S1 and S2 are each produced in multiple numbers in a wafer state at a time, followed by dicing into individual pieces, and then fixed to the ceramic package 51 using a die paste (not illustrated). Thereafter, electrode pads 37a to 37d and 47a to 47d are connected to their corresponding package electrodes 54 through the bonding wires 55 using a wire bonding machine. As the material of the bonding wire 55, a metal having low resistance, such as Au, Al, or Cu is preferably used.

Finally, adhesive resin (not illustrated) or the like is used to fix the lid 52 having the outside air vent holes 53 to the ceramic package 51. Although a substance contained in the adhesive resin is turned into gas during heating/curing of the adhesive resin (not shown), the gas is easily discharged outside the package through the vent holes 53, so that the first and second sensor parts S1 and S2 are hardly affected.

The thus accomplished the sensor part S is connected to the signal processing circuit 20 or a power supply through the external terminal 56. The correction resistor R1 may be incorporated in the signal processing circuit 20, housed in the ceramic package 51, or provided on a circuit board on which the signal processing circuit 20 is mounted.

The configuration of the gas sensor 10A according to the present embodiment has been described. Next, the operation of the gas sensor 10A according to the present embodiment will be described.

The gas sensor 10A according to the present embodiment utilizes a significant difference between the heat conductivity of the $CO_2$ gas and that of air to take out a change in the heat dissipation characteristics of the thermistors Rd1 and Rd2 according to the $CO_2$ gas concentration as the detection signal Vout1. However, the heat conductivity of the measurement atmosphere changes according not only to the $CO_2$ gas concentration but also to humidity, i.e., the vapor concentration, so that the influence of humidity may cause a measurement error. Thus, the gas sensor 10A according to the present embodiment adjusts the resistance value of the correction resistor R1 so as to make an error component of the first thermistor Rd1 due to humidity and an error component of the second thermistor Rd2 due to humidity coincide with each other to cancel a change in the detection signal Vout1 based on humidity.

Figure 4:
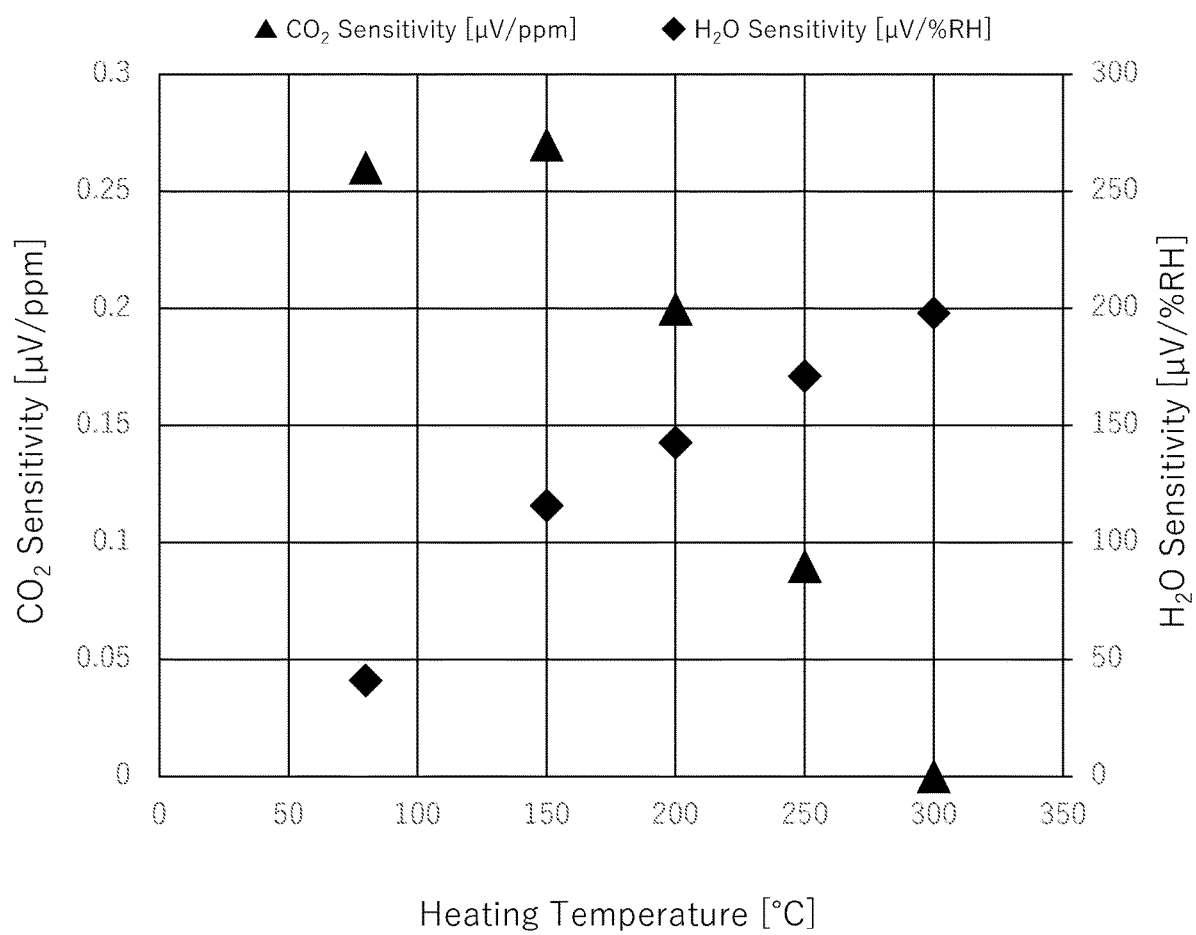
FIG. 4 is a graph illustrating the relationship between the heating temperature and sensitivity of the thermistors Rd1 and Rd2.

FIG. 4 is a graph illustrating the relationship between the heating temperature and sensitivity of the thermistors Rd1 and Rd2.

As illustrated in FIG. 4, when the heating temperature of the thermistors Rd1 and Rd2 is 150° C. or lower, it is possible to obtain a sufficiently high sensitivity with respect to the $CO_2$ gas concentration; while when the heating temperature exceeds 150° C., the sensitivity with respect to the $CO_2$ gas concentration decreases, and when the heating temperature reaches 300° C., the sensitivity with respect to the $CO_2$ gas concentration becomes substantially 0. Actually, even when the heating temperature is 300° C., there is a slight sensitivity with respect to the $CO_2$ gas concentration; however, it is significantly lower than (about 1/10 of) that when the heating temperature is 150° C. and can thus be substantially ignored.

Taking the above into consideration, in the gas sensor 10A according to the present embodiment, the first thermistor Rd1 is heated to 150° C. to sufficiently increase the sensitivity (first sensitivity) with respect to the $CO_2$ gas concentration, and the second thermistor Rd2 is heated to 300° C. to reduce the sensitivity (third sensitivity) with respect to the $CO_2$ gas concentration to substantially 0. Since the first and second thermistors Rd1 and Rd2 are connected in series to each other, the level of the detection signal Vout1 represents the $CO_2$ gas concentration when there is no influence of humidity.

On the other hand, the sensitivity (second sensitivity) with respect to the humidity when the heating temperature of the first thermistor Rd1 is 150° C. and the sensitivity (fourth sensitivity) with respect to the humidity when the heating temperature of the second thermistor Rd2 is 300° C. differ from each other. Specifically, the second sensitivity is about 120 μV/% RH, while the fourth sensitivity is about 200 μV/% RH. Therefore, the influence of humidity is reflected on the detection signal Vout1 when the first and second thermistors Rd1 and Rd2 are simply connected in series.

Thus, in the gas sensor 10A according to the present embodiment, the correction resistor R1 is connected in parallel to the second thermistor Rd2 so as to cancel a change in the detection signal Vout1 according to humidity. Assuming that the second sensitivity is a, the fourth sensitivity is b, and the resistance value of the second thermistor Rd2 heated to 300° C. is Rd2, the resistance value of the correction resistor R1 is set to: R1=(b/a)×Rd2, whereby it is possible to substantially cancel a change in the detection signal Vout1 according to humidity. When this expression is applied to the above-described example, R1 may be set to (200/120)×Rd2=(5/3)×Rd2.

Thus, the influence that humidity has on the first thermistor Rd1 and the influence that humidity has on the second thermistor Rd2 effectively coincide with each other, so that the detection signal Vout1 does not change even with a change in humidity. That is, the level of the detection signal Vout1 is determined by the $CO_2$ gas concentration.

Figure 5:
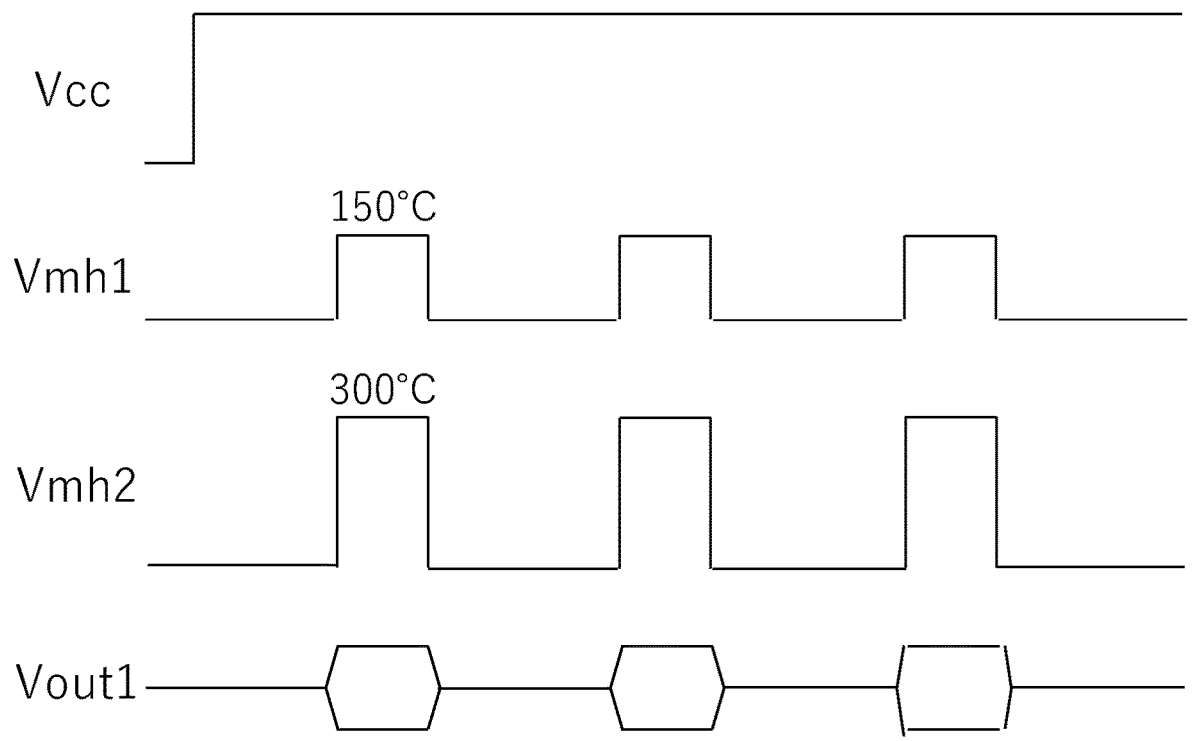
FIG. 5 is a timing chart illustrating an example of the waveforms of the control voltages Vmh1 and Vmh2.

FIG. 5 is a timing chart illustrating an example of the waveforms of the control voltages Vmh1 and Vmh2. As illustrated in FIG. 5, in the present embodiment, the control voltage Vmh1 and control voltage Vmh2 are simultaneously brought to an active level to simultaneously heat the first heater resistor MH1 and second heater resistor MH2. Then, the detection signal Vout1 is sampled at the timing when the control voltages Vmh1 and Vmh2 are activated, whereby it is possible to measure the $CO_2$ gas concentration without necessity of computation processing for canceling the influence of humidity.

Figure 6A:
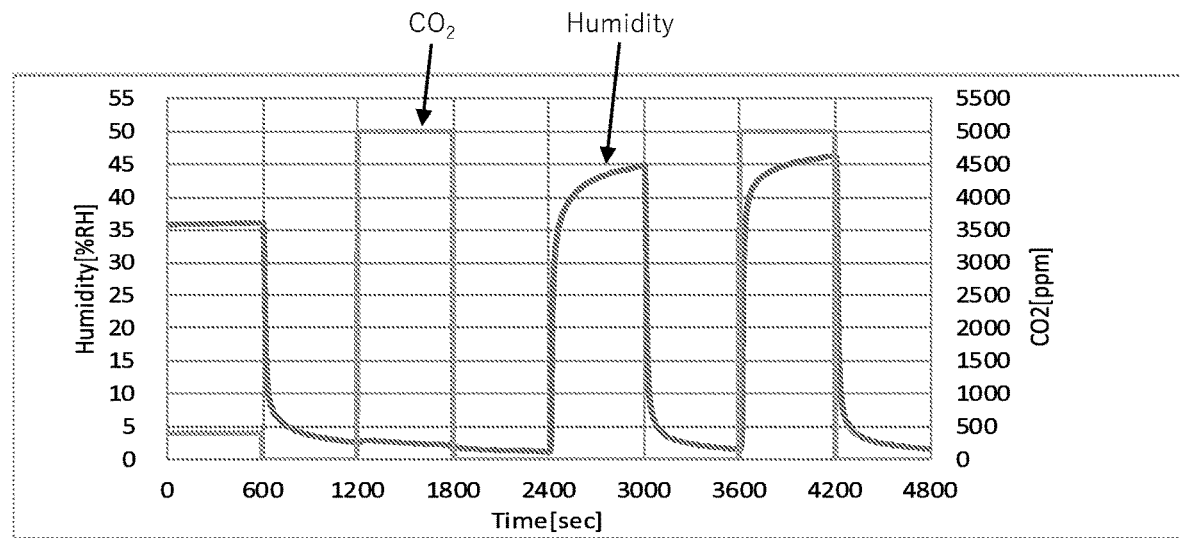
FIGS. 6A and 6B are graphs illustrating actual measurement values, where
Figure 6B:
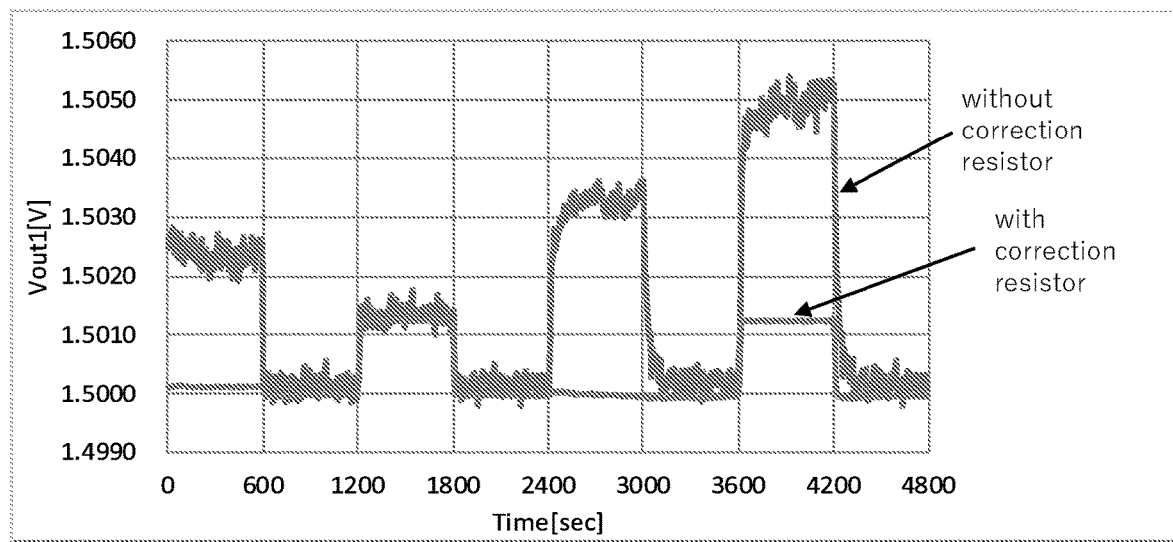

FIGS. 6A and 6B are graphs illustrating actual measurement values. FIG. 6A illustrates a change in the $CO_2$ gas and a change in humidity, and FIG. 6B illustrates a change in the detection signal Vout1. As illustrated in FIG. 6, it can be found that when the correction resistor R1 is not employed, the level of the detection signal Vout1 significantly changes depending on humidity, while when the correction resistor R1 is employed, the influence of humidity is substantially completely canceled from the detection signal Vout1.

As described above, in the gas sensor 10A according to the present embodiment, the two thermistors Rd1 and Rd2 different in heating temperature are connected in series to each other, and the correction resistor R1 is connected parallel to the second thermistor Rd2, so that the level of the detection signal Vout1 appearing at the connection point between the first and second thermistors Rd1 and Rd2 accurately represents the $CO_2$ gas concentration without being influenced by humidity. Thus, it is possible to directly measure the $CO_2$ gas concentration without through computation processing for canceling the influence of humidity.

Figure 7:
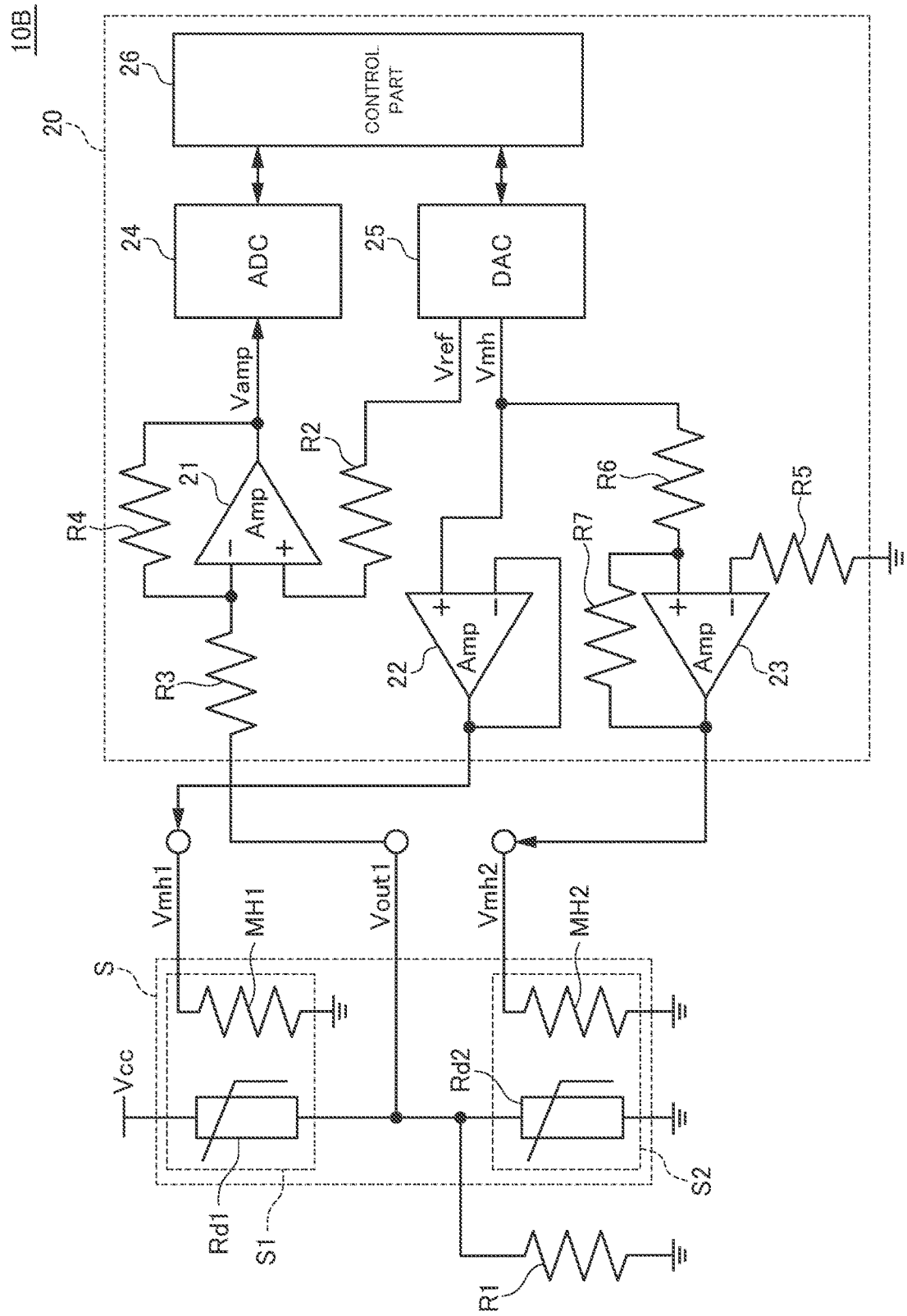
FIG. 7 is a circuit diagram illustrating the configuration of a gas sensor 10B according to a second embodiment of the present invention.

FIG. 7 is a circuit diagram illustrating the configuration of a gas sensor 10B according to a second embodiment of the present invention.

As illustrated in FIG. 7, the gas sensor 10B according to the present embodiment differs from the gas sensor 10A according to the first embodiment illustrated in FIG. 1 in that a common control voltage Vmh is supplied in common to the differential amplifiers 22 and 23 and that the differential amplifier 23 does not serve as a voltage follower and is gain-adjusted using resistors R5 to R7. Other configurations are the same as those of the gas sensor 10A according to the first embodiment, so the same reference numerals are given to the same elements, and overlapping description will be omitted.

The resistors R5 to R7 are elements for adjusting the gain of the differential amplifier 23. For example, when the resistance values of the resistors R5 to R7 are set such that R5=R6=R7, Vmh2=2×Vmh1 can be satisfied. That is, it is possible to generate two mutually different control voltages Vmh1 and Vmh2 using the common control voltage Vmh.

As a result, even when the level of the common control voltage Vmh temporarily changes due to, e.g., fluctuation of a power supply potential, both the control voltages Vmh1 and Vmh2 fluctuate simultaneously in conjunction with the common control voltage Vmh, thereby canceling the influence due to the fluctuations of the control voltages Vmh1 and Vmh2. Therefore, the level of the detection signal Vout1 does not substantially change even with a fluctuation of the common control voltage Vmh. Thus, according to the present embodiment, it is possible to measure the $CO_2$ gas concentration more stably.

Figure 8:
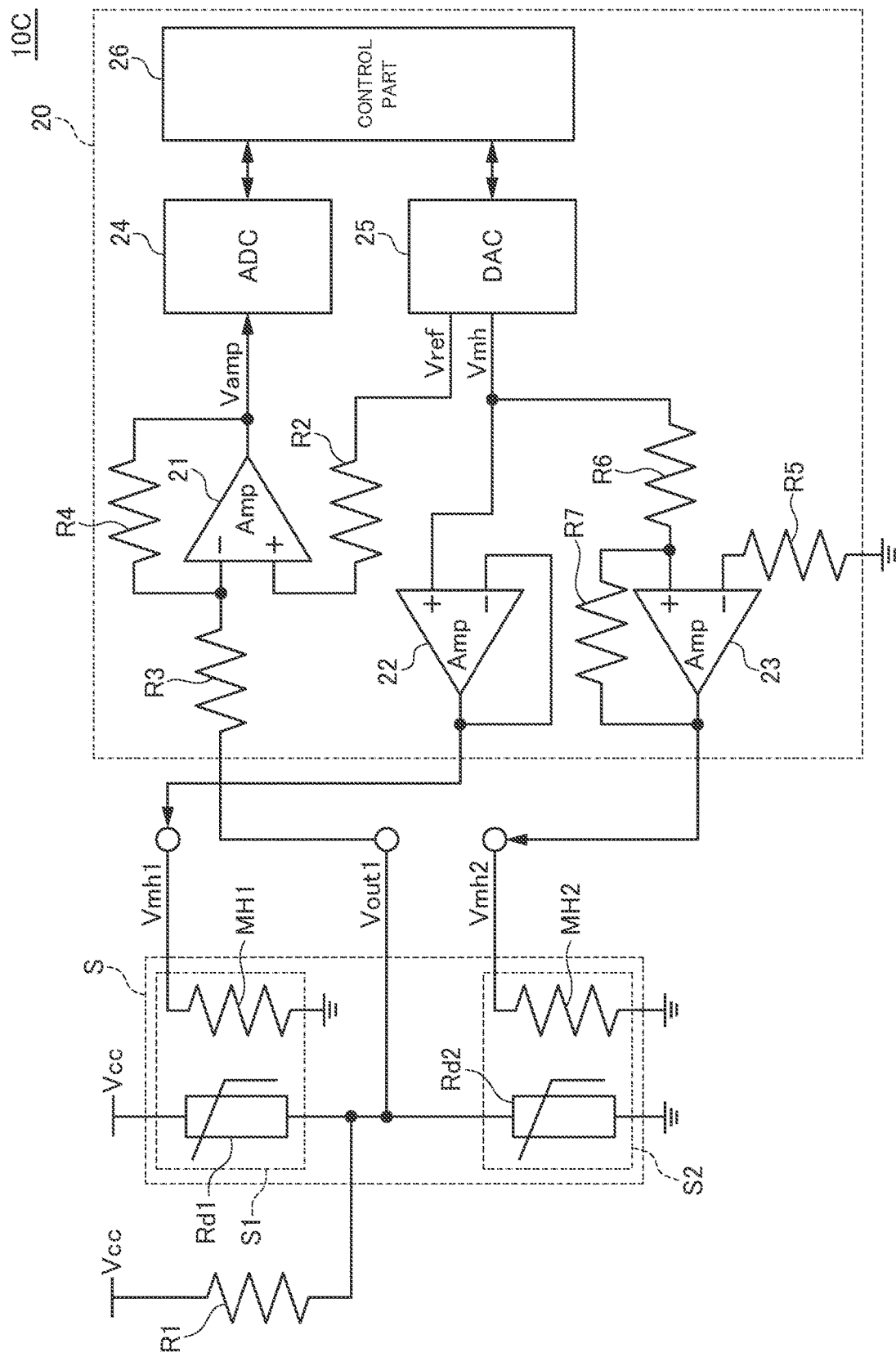
FIG. 8 is a circuit diagram illustrating the configuration of a gas sensor 10C according to a third embodiment of the present invention.

FIG. 8 is a circuit diagram illustrating the configuration of a gas sensor 10C according to a third embodiment of the present invention.

As illustrated in FIG. 8, the gas sensor 10C according to the present embodiment differs from the gas sensor 10B according to the second embodiment illustrated in FIG. 7 in that the correction resistor R1 is connected in parallel to the first thermistor Rd1. Other configurations are the same as those of the gas sensor 10B according to the second embodiment, so the same reference numerals are given to the same elements, and overlapping description will be omitted.

As exemplified in the present embodiment, when the sensitivity (second sensitivity) of the first thermistor Rd1 with respect to humidity is higher than the sensitivity (fourth sensitivity) of the second thermistor Rd2 with respect to humidity, the correction resistor R1 may be connected parallel to the first thermistor Rd1 so as to effectively reduce the second sensitivity.

Figure 9:
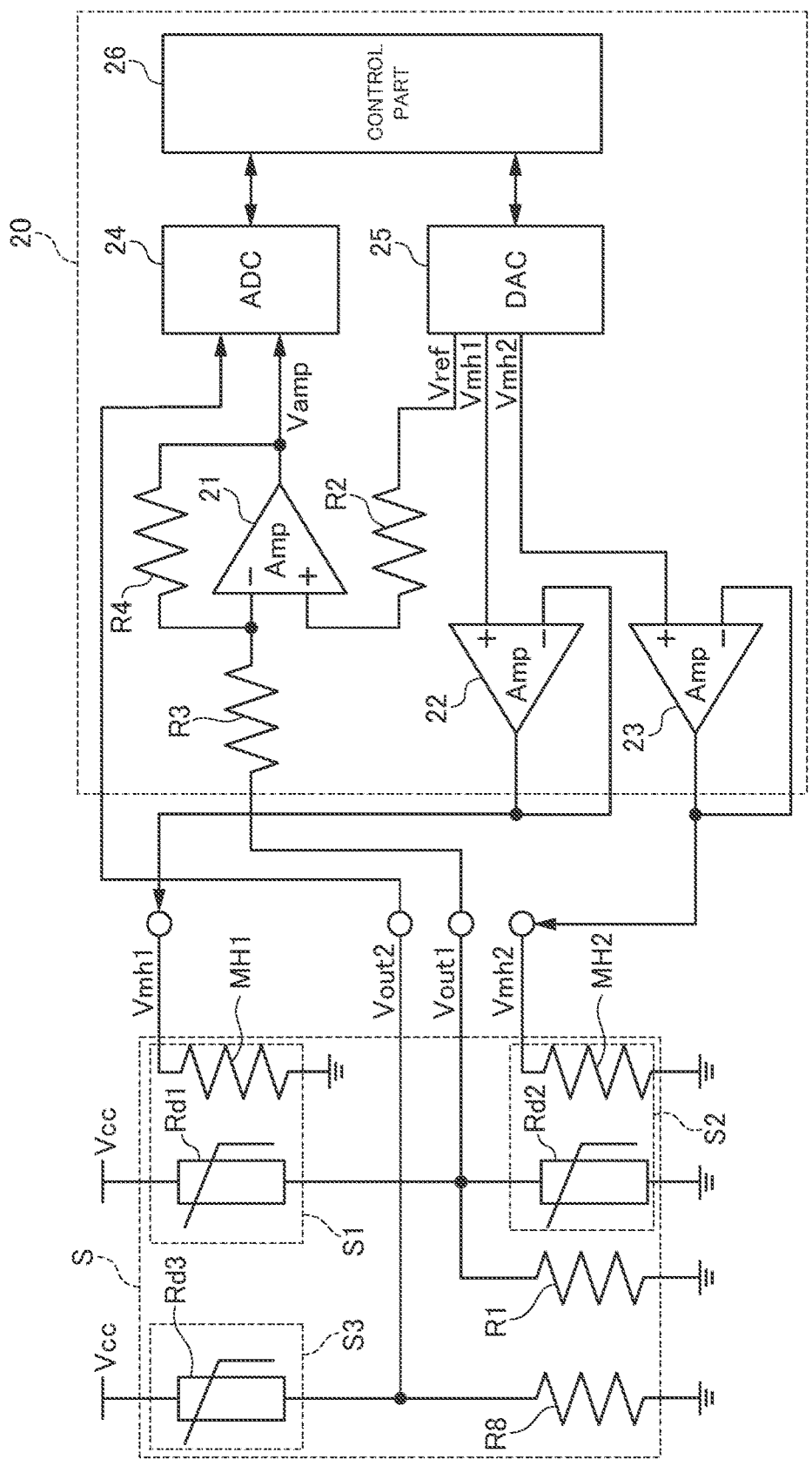
FIG. 9 is a circuit diagram illustrating the configuration of a gas sensor 10D according to a fourth embodiment of the present invention.

FIG. 9 is a circuit diagram illustrating the configuration of a gas sensor 10D according to a fourth embodiment of the present invention.

As illustrated in FIG. 9, the gas sensor 10D according to the present embodiment differs from the gas sensor 10A according to the first embodiment illustrated in FIG. 1 in that a third sensor part S3 as a temperature sensor and a resistor R8 are additionally provided in the sensor part S. The third sensor part S3 includes a third thermistor Rd3, and the third thermistor Rd3 and the resistor R8 are connected in series to each other between a wiring supplied with a power supply potential Vcc and a wiring supplied with a ground potential GND. A temperature signal Vout2 is output from a connection point between the third thermistor Rd3 and the resistor R8. The temperature signal Vout2 is supplied to the AD converter 24. Other circuit configurations are the same as those of the gas sensor 10A according to the first embodiment, so the same reference numerals are given to the same elements, and overlapping description will be omitted.

Figure 10:
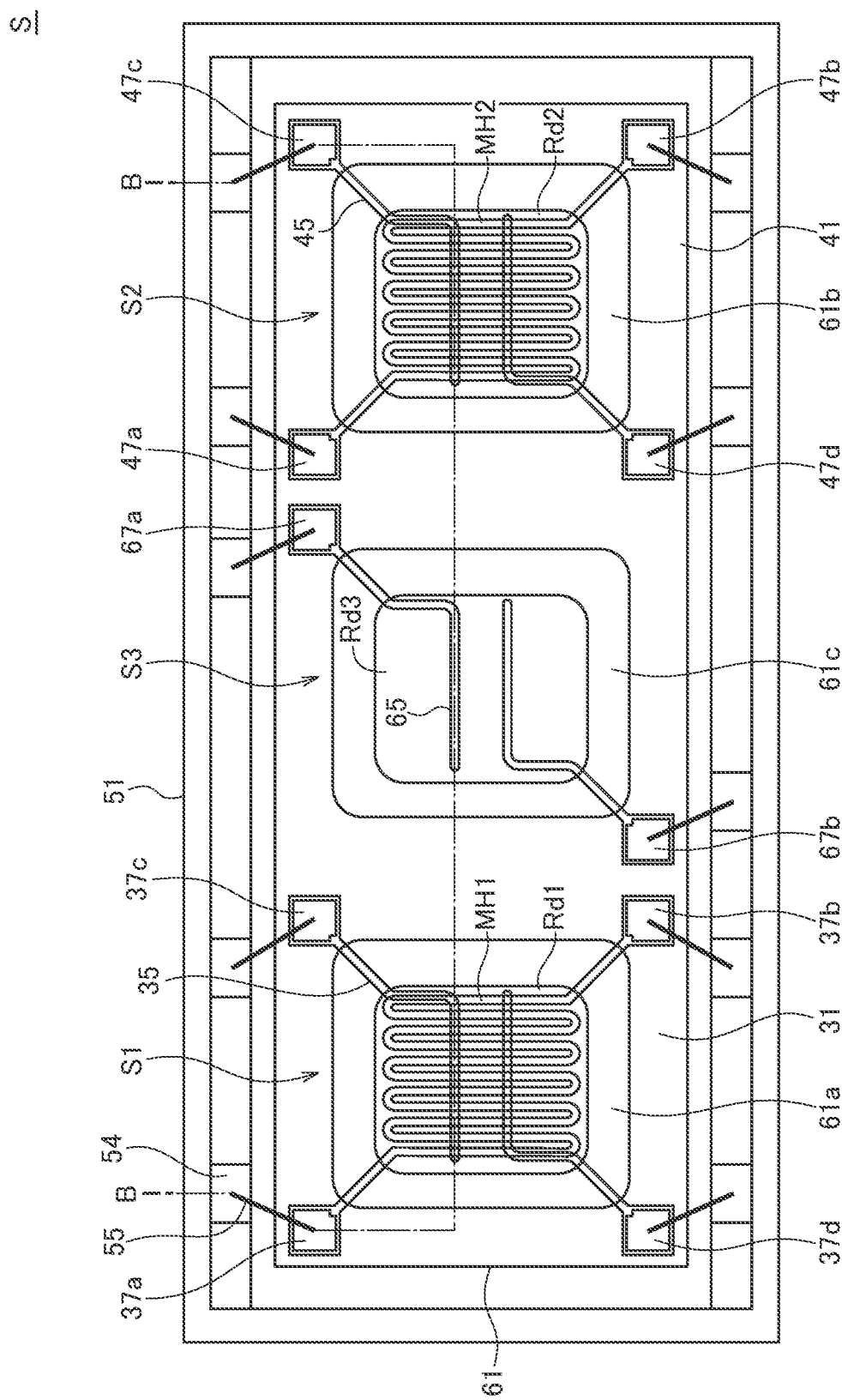
FIG. 10 is a top view for explaining the configuration of the sensor part S in the fourth embodiment of the present invention.
Figure 11:
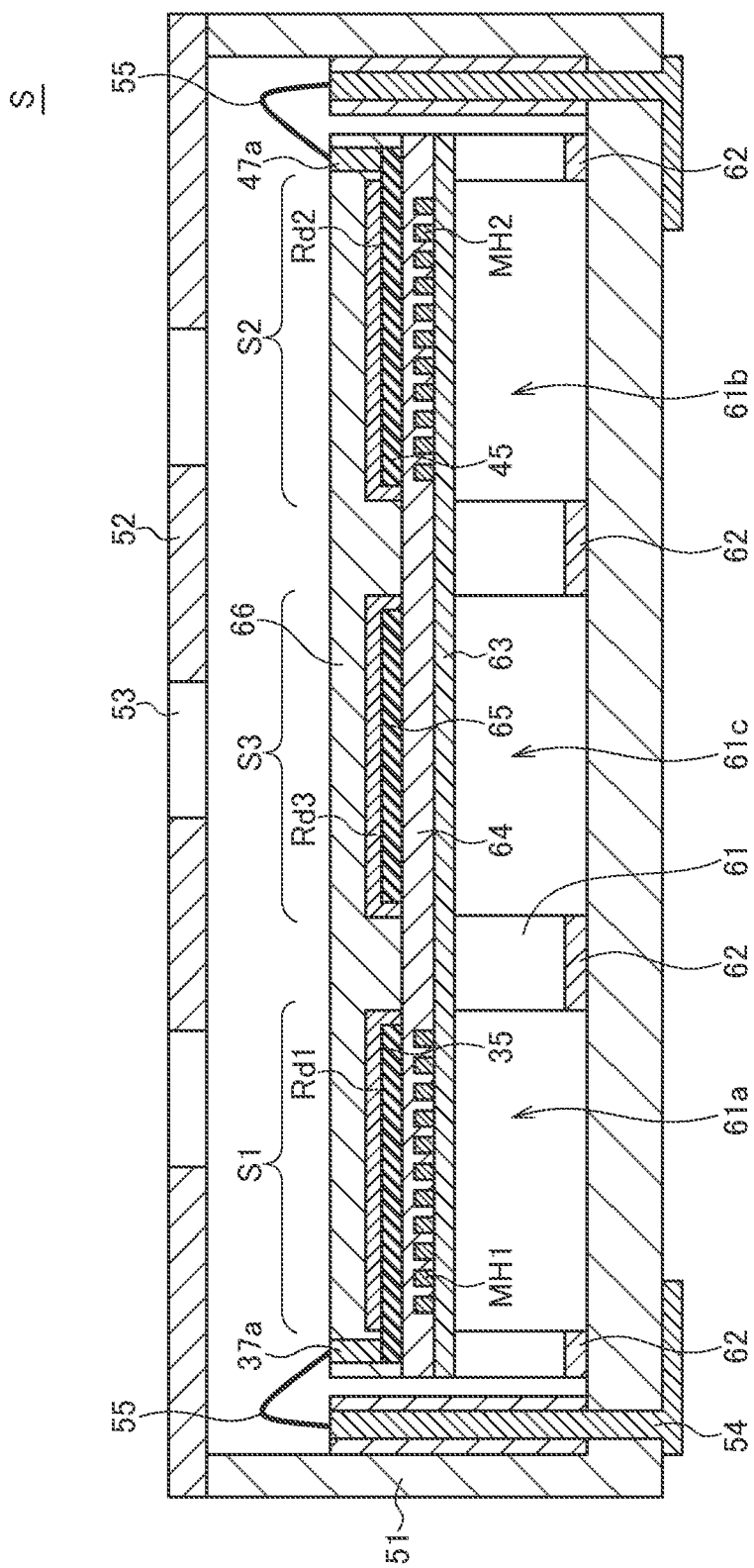
FIG. 11 is a cross-sectional view taken along line B-B in FIG. 10.

FIG. 10 is a top view for explaining the configuration of the sensor part S in the present embodiment. FIG. 11 is a cross-sectional view taken along line B-B in FIG. 10. The drawings are schematic, and the relation between thickness and plane dimension, the ratio between the thicknesses of devices, and the like may be different from those in the actual structure within a range in which the effect of the present embodiment can be obtained.

As illustrated in FIGS. 10 and 11, in the present embodiment, the third sensor part S3 is disposed between the first sensor part S1 and the second sensor part S2. Although not particularly limited, in the present embodiment, the three sensor parts S1 to S3 are integrated on a single substrate 61. The substrate 61 has formed therein three cavities 61a to 61c corresponding to the three sensor parts S1 to S3.

The substrate 61 has insulating films 62 and 63, a heater protective film 64, the third thermistor Rd3 and a thermistor electrode 65 which are provided on the heater protective film 64 at a position overlapping the cavity 61c, and a thermistor protective film 66 that covers the first thermistors Rd1 to Rd3 and thermistor electrodes 35, 45, and 65. As illustrated in FIG. 10, both ends of the thermistor electrode 65 constituting the third thermistor Rd3 are connected respectively to electrode pads 67a and 67b provided on the surface of the thermistor protective film 66. The electrode pads 67a and 67b are each connected to a package electrode 54 attached to a ceramic package 51 through a bonding wire 55. Other basic configurations are the same as those illustrated in FIGS. 2 and 3, so the same reference numerals are given to the same elements, and overlapping description will be omitted.

The above is the configuration of the gas sensor 10D according to the present embodiment. As described above, in the gas sensor 10D according to the present embodiment, the three sensor parts S1 to S3 are integrated on the single substrate 61, so that it is possible to additionally provide the third sensor part S3 serving as a temperature sensor without unnecessarily increasing the number of parts. In addition, by disposing the third sensor part S3 in the center of the gas sensor 10D, the distance between the first sensor part S1 and the second sensor part S2 can be increased, making it possible to reduce mutual thermal interference. That is, the first sensor part 51 and the second sensor part S2 differ in heating temperature and are heated simultaneously, so that thermal interference may occur when the distance therebetween is small. However, in the present embodiment, the sensor part S3 is disposed between the first sensor part S1 and the second sensor part S2, so that thermal interference between the first sensor part S1 and the second sensor part S2 is reduced, allowing more accurate measurement.

Figure 12:
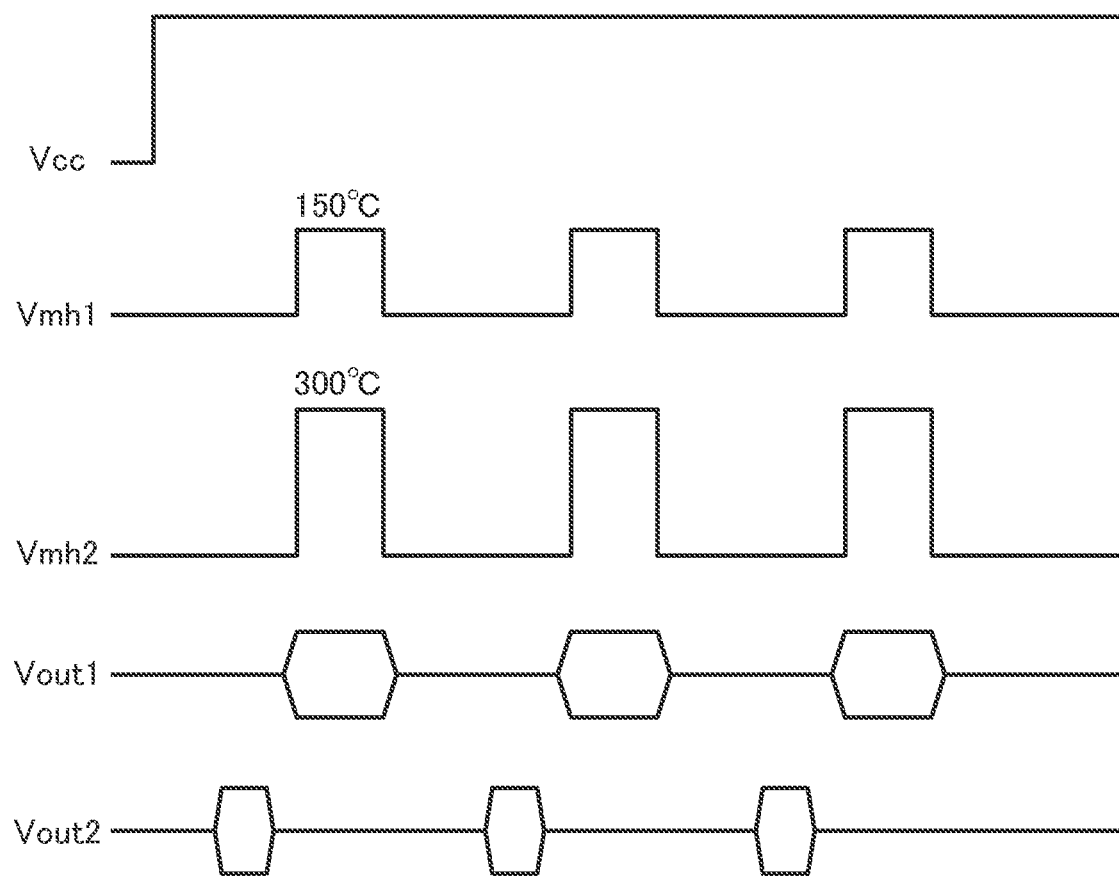
FIG. 12 is a timing chart for explaining a timing at which the temperature signal Vout2 is sampled.

FIG. 12 is a timing chart for explaining a timing at which the temperature signal Vout2 is sampled. As illustrated in FIG. 12, also in the present embodiment, the control voltage Vmh1 and the control voltage Vmh2 are simultaneously brought to an active level to simultaneously heat the first heater resistor MH1 and second heater resistor MH2. Then, the detection signal Vout1 is sampled at the timing when the control voltages Vmh1 and Vmh2 are activated, and the temperature signal Vout2 is sampled at a timing before the activation of the control voltages Vmh1 and Vmh2. This makes it possible to accurately measure an environmental temperature using the third sensor part S3 without being influenced by heating by the first and second heater resistors MH1 and MH2.

Figure 13:
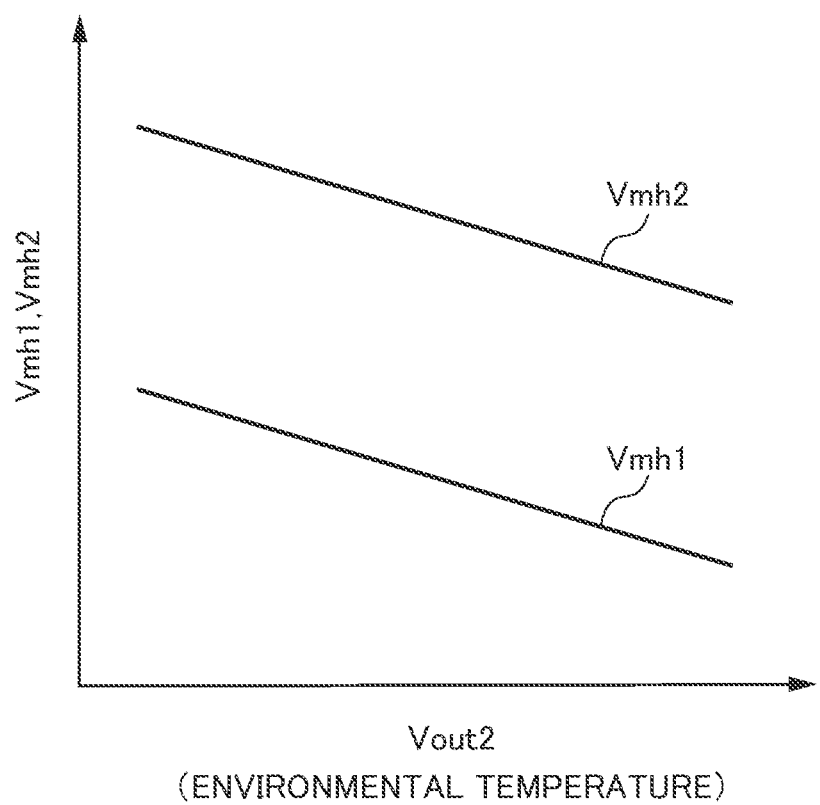
FIG. 13 is a graph illustrating the relationship between an environmental temperature and control voltages Vmh1, Vmh2.

The temperature signal Vout2 is supplied to the AD converter 24 illustrated in FIG. 9. The temperature signal Vout2 supplied to the AD converter 24 is converted into a digital signal and is supplied to the control part 26. The control part stores therein mathematical expressions or tables representing the relationship between an environmental temperature and the control voltages Vmh1, Vmh2, and the control voltages Vmh1 and Vmh2 are corrected thereby. FIG. 13 is a graph illustrating the relationship between an environmental temperature and control voltages Vmh1, Vmh2. As illustrated in FIG. 13, the control part 26 corrects the control voltages Vmh1 and Vmh2 so that the levels of the control voltages Vmh1 and Vmh2 decrease as the environmental temperature rises. Thus, by changing the levels of the control voltages Vmh1 and Vmh2 according to the current environmental temperature obtained as the temperature signal Vout2, it is possible to set heating temperatures by the first and second heater resistors MH1 and MH2 to values substantially the same as designed temperatures irrespective of the current environmental temperature.

As described above, in the gas sensor 10D according to the present embodiment, not only the control voltages Vmh1 and Vmh2 are corrected based on the temperature signal Vout2, but also the sensor part S3 is disposed between the first sensor part S1 and the second sensor part S2, so that thermal interference between the first sensor part S1 and the second sensor part S2 is reduced. This allows the $CO_2$ gas concentration to be measured more accurately.

In addition, the third sensor part S3 is disposed on the same chip as the first and second sensor parts S1 and S2, so that the third sensor part S3 can measure substantially the same environmental temperature as an environmental temperature to which the first sensor part S1 and second sensor part S2 are subject. This allows very accurate temperature measurement, making it possible to set heating temperatures by the first and second heater resistors MH1 and MH2 to values substantially the same as designed temperatures.

It is apparent that the present invention is not limited to the above embodiments, but may be modified and changed without departing from the scope and spirit of the invention.

For example, although the above description has been made with the example in which the first and second gases are $CO_2$ gas and vapor, respectively, the present invention is not limited to this. Further, the sensor part to be employed in the present invention may not necessarily be the heat conduction type sensor but may be a sensor of other types, such as a contact combustion type.

REFERENCE SIGNS LIST 10A-10D gas sensor
20 signal processing circuit
21-23 differential amplifier
24 AD converter
25 DA converter
26 control part
31, 41, 61 substrate
31a, 41a, 61a-61c cavity 32, 33, 42, 43, 62, 63 insulating film
34, 44, 64 heater protective film
35, 45, 65 thermistor electrode
36, 46, 66 thermistor protective film
37a-37d, 47a-47d, 67a, 67b electrode pad
51 ceramic package
52 lid
53 vent hole
54 package electrode
55 bonding wire
56 external terminal
MH1, MH2 heater resistor
R1 correction resistor
R2-R8 resistor
Rd1-Rd3 thermistor
S sensor part
S1 first sensor part
S2 second sensor part
S3 third sensor part

What is claimed is:

1. A gas sensor comprising:
a first thermistor having a resistance value that changes according to a concentration of a first gas with a first sensitivity and changes according to a concentration of a second gas with a second sensitivity;
a second thermistor connected in series to the first thermistor, the second thermistor having a resistance value that changes according to a concentration of the first gas with a third sensitivity that is lower than the first sensitivity and changes according to a concentration of the second gas with a fourth sensitivity that is different from the second sensitivity; and
a correction resistor connected in parallel with the first or second thermistor to cancel a change in potential at a connection point between the first and second thermistors according to the concentration of the second gas,
wherein the first thermistor is heated to a first temperature by a first heater,
wherein the second thermistor is heated to a second temperature different from the first temperature by a second heater,
wherein the gas sensor further comprises:
a third thermistor disposed between the first thermistor and the second thermistor; and
a control part that changes first and second control voltages to be supplied respectively to the first and second heaters according to a temperature signal supplied from the third thermistor.

2. The gas sensor as claimed in claim 1,
wherein the fourth sensitivity is higher than the second sensitivity, and
wherein the correction resistor is connected in parallel to the second thermistor.

3. The gas sensor as claimed in claim 2, wherein, assuming that the second sensitivity is a, the fourth sensitivity is b, and the resistance value of the second thermistor heated to the second temperature is Rd2, the resistance value R1 of the correction resistor is defined as: $R1=(b/a) \times Rd2$.

4. The gas sensor as claimed in claim 1, further comprising:
a first amplifier that receives a common control voltage and applies a first control voltage to the first heater; and
a second amplifier that receives the common control voltage and applies a second control voltage to the second heater.

5. The gas sensor as claimed in claim 1, wherein the third sensitivity is 1/10 or less of the first sensitivity.

6. The gas sensor as claimed in claim 1, wherein the first thermistor and second thermistor are housed in a same package.

7. The gas sensor as claimed in claim 1, wherein each of the first and second thermistors constitutes a heat conduction type sensor.

8. The gas sensor as claimed in claim 7, wherein the first gas is a $CO_2$ gas, and the second gas is vapor.

* * * * *